United States Patent
Park et al.

(10) Patent No.: US 7,156,731 B2
(45) Date of Patent: Jan. 2, 2007

(54) RESOLUTION OF CHIRAL COMPOUNDS USING AMINOCYCLOPENTADIENYL RUTHENIUM CATALYSTS

(75) Inventors: Jaiwook Park, Pohang (KR); Mahn-Joo Kim, Pohang (KR); Jun Ho Choi, Pohang (KR); Yangsoo Ahn, Seoul (KR)

(73) Assignee: Postech Foundation (KR)

( * ) Notice: Subject to any disclaimer, the term of this patent is extended or adjusted under 35 U.S.C. 154(b) by 291 days.

(21) Appl. No.: 10/507,727

(22) PCT Filed: May 17, 2002

(86) PCT No.: PCT/KR02/00926

§ 371 (c)(1),
(2), (4) Date: Sep. 13, 2004

(87) PCT Pub. No.: WO03/076384

PCT Pub. Date: Sep. 18, 2003

(65) Prior Publication Data

US 2005/0130282 A1 Jun. 16, 2005

(30) Foreign Application Priority Data

Mar. 14, 2002 (KR) .............................. 2002-13832

(51) Int. Cl.
*G07D 1/00* (2006.01)
*C07F 15/00* (2006.01)
*C07F 17/02* (2006.01)

(52) U.S. Cl. .......................... 453/41; 556/137; 556/16

(58) Field of Classification Search ................. 435/41; 556/137, 16

See application file for complete search history.

(56) References Cited

OTHER PUBLICATIONS

Jeong Hwan Koh, Hyun Min Jung, Mahn-Joo Kim and Jaiwook Park Enzymatic resolution of secondary alcohols coupled with ruthenium-catalyzed racemization without hydrogen mediator Tetrahedron Letters 40 (1999) 6281-6284.*

* cited by examiner

*Primary Examiner*—Samuel A Barts
*Assistant Examiner*—Lalitha Nagubandi
(74) *Attorney, Agent, or Firm*—Anderson Kill & Olick, PC

(57) ABSTRACT

A chiral compound, particularly a chiral secondary alcohol, can be efficiently resolved under a mild condition by acylation with an alkenyl acetate in the presence of a novel aminocyclopentadienyl ruthenium complex, an enzyme catalyst, and a base.

11 Claims, No Drawings

RESOLUTION OF CHIRAL COMPOUNDS USING AMINOCYCLOPENTADIENYL RUTHENIUM CATALYSTS

FIELD OF THE INVENTION

The present invention relates to a high-yield resolution method for obtaining an enantiometrically pure compound using a novel aminocyclopentadienyl ruthenium catalyst.

BACKGROUND OF THE INVENTION

The resolution of one enantiomer from a racemic mixture is often required in pharmaceutical and other chemical industries. Such resolution is generally conducted by selectively acylating the desired enantiomer with an acylating agent in the presence of an enzyme catalyst while the other enantiomer is simultaneously racemized in situ by the action of a metal catalyst. In such a process, ruthenium complexes such as [(p-cymene)RuCl$_2$]$_2$ and ($\eta^5$-Ph$_4$C$_4$CO)$_2$H($\mu$-H)(CO)$_4$Ru$_2$ (Shvo catalyst) have been conventionally used as a racemization catalyst, and an aryl acetate, as an acylating agent in the presence of a lipase catalyst.

However, the ruthenium cymene complex catalyzes the racemization very slowly at room temperature, and the Shvo catalyst which exists in the form of a dimer must be activated at a high temperature and it also requires the use of a hydrogen-transfer agent, e.g., the corresponding ketone to the alcohol in case a chiral alcohol is to be racemized (Y. Shvo et al, *Organometallics,* 8, 162, 1989).

Further, the aryl acetate used in the prior resolution method as an acylating agent generates an aryl alcohol as a by-product which is difficult to separate from the reaction product (see M. J. Kim et al, *Organic Letters* 2, 2377 (2000)). The use of an alkenyl acetate in place of an aryl acetate has also been attempted, but in its presence, oxidation of the target chiral alcohol occurs to some extent in the presence of the above-mentioned metal catalysts.

SUMMARY OF THE INVENTION

Accordingly, it is an object of the present invention to provide an improved process for resolving a chiral compound, particularly a chiral alcohol, by way of employing a novel metal catalyst which is effective for the racemization of the unwanted enantiomer under a mild condition and does not oxidize the chiral alcohol when an alkenyl acetate is used as an acylating agent.

In accordance with one aspect of the present invention, there is provided a method of resolving a chiral compound comprising reacting the chiral compound with an acylating agent in the presence of a metal catalyst, an enzyme catalyst, and a base, characterized in that the metal catalyst is a ruthenium complex of formula (I):

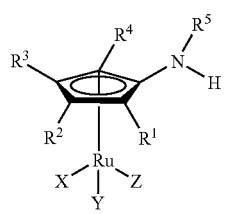

(I)

wherein:
R$^1$, R$^2$, R$_3$ and R$^4$ are each independently phenyl, substituted phenyl or C$_{1-5}$ alkyl;
R$^5$ is hydrogen, phenyl, substituted phenyl, C$_{1-5}$ alkyl, substituted C$_{1-5}$ alkyl, C$_{3-7}$ cycloalkyl, C$_{2-5}$ alkenyl or C$_{2-5}$ alkynyl; and
X, Y and Z are each independently hydrogen, halogen, carbonyl or PR$^5$$_3$.

DETAILED DESCRIPTION OF THE INVENTION

In the ruthenium complex of Formula(I) of the present invention, the substituent of the substituted phenyl is at least one selected from the group consisting of C$_{1-5}$ alkyl, cycloalkyl, alkenyl, alkynyl, alkoxy, halogen, nitro, nitroso, amino, aminocarbamyl, hydroxy, mercapto and C$_{1-5}$ alkylthio, and the substituent of the substituted C$_{1-5}$ alkyl is at least one selected from the group consisting of aryl, C$_{1-5}$ alkoxy, halogen, nitro, nitroso, amino, aminocarbamyl, hydroxy, mercapto and C$_{1-5}$ alkylthio.

In Formula(I) of the present invention, R$^1$, R$^2$, R$^3$ or R$^1$ is preferably phenyl or a C$_{1-5}$ alkyl group, R$^5$ is preferably hydrogen, phenyl or a substituted phenyl group, a C$_{1-5}$ alkyl or substituted C$_{1-5}$ alkyl group or a C$_{3-7}$ cycloalkyl group, and X, Y and Z substituents are each preferably hydrogen, halogen, carbonyl, or a phosphine group.

The ruthenium complex of Formula (I) of the present invention may be prepared according to Reaction Scheme A:

Reaction Scheme A

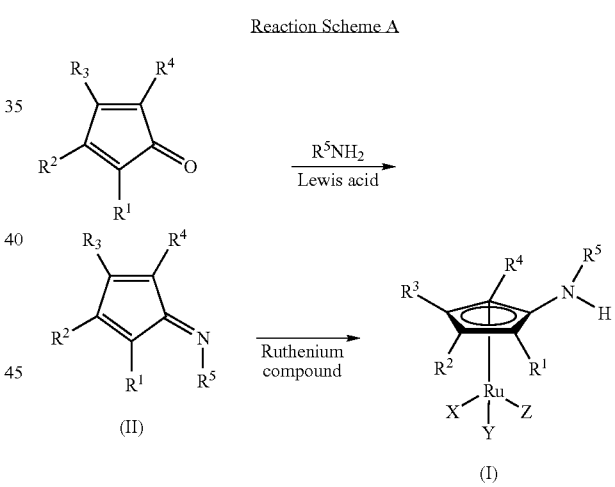

wherein:
R$^1$, R$^2$, R$^3$, R$^4$, R$^5$, X, Y and Z have the same meanings as defined in formula(I) above.

Namely, a cyclopentadienone derivative such as tetraphenylcyclopentadienone is reacted in an aprotic solvent with a primary amine in the presence of a Lewis acid to obtain an imine compound of Formula(II) (Step 1). Then, the imine compound of Formula(II) is reacted with a ruthenium compound having X, Y and Z groups, such as Ru$_3$(CO)$_{12}$, RuCl$_2$(CO)$_2$(PR$^5$$_3$)$_2$, [RuCl$_2$(CO)$_3$]$_2$, RuCl$_2$(PR$^5$$_3$)$_3$, or RuCl$_3$, in a solvent, preferably a haloform, to obtain the ruthenium complex of Formula (I) of the present invention (Step 2).

Representative examples of the primary amine(R$^5$—NH$_2$) used in Step 1 are ammonia, methylamine, ethylamine, propylamine, butylamine, pentylamine, isobutylamine, isopropylamine, t-butylamine, cyclopropylamine, cyclobutylamine, cyclopentylamine, aniline, toluidine and benzylamine. Also used in the present invention is a conventional Lewis acid, commonly known in the art, including $TiCl_4$, $AlCl_3$, $BF_3$ and $SnCl_4$.

Representative examples of the aprotic solvent used in Step 1 are toluene, benzene, hexane, oxane, tetrahydrofuran, diethyl ether, diisopropyl ether, t-butylmethyl ester, ethyl acetate, acetonitrile, acetone, dichloromethane, chloroform and carbon tetrachloride.

In Step 1, the primary amine, the Lewis acid and the aprotic solvent may be used in amounts of 1 to 7 molar equivalents, 0.1 to 3 molar equivalents and 2 to 20 folds (w/w), respectively, based on the starting cyclopentadienone derivative, and the reaction may be conducted at a temperature in the range of 50° C. to 150° C.

In Step 2, the solvent may be chloroform, bromoform or fluoroform, and the amount of the imine compound of Formula(II) may be 1 to 3 molar equivalents based on the ruthenium compound. The reaction may be conducted at a temperature in the range of 40° C. to 120° C.

The inventive method of resolving a chiral compound, e.g., a chiral secondary alcohol can be advantageously conducted with an alkenyl acetate of the following formula as an acylating agent:

$$CH_3COOR^6$$

wherein:

$R^6$ is a $C_{2-5}$ alkenyl or substituted $C_{2-5}$ alkenyl; the substituent of the substituted alkenyl is at least one selected from the group consisting of aryl, $C_{1-5}$ alkoxy, halogen, nitro, nitroso, amino, aminocarbamyl, hydroxy, mercapto and $C_{1-5}$ alkylthio.

Although conventional aryl acetate may be used in the present invention as an acylating agent, the use of such an alkenyl acetate instead of conventional aryl acetate is much more desirable in terms of simpleness of product separation and the product oxidation problem observed when an alkenyl acetate is used with a conventional metal catalyst is avoided when the present novel ruthenium catalyst is employed.

The resolution of a chiral secondary alcohol according to the present invention may be illustrated by Reaction Scheme B.

Reaction Scheme B

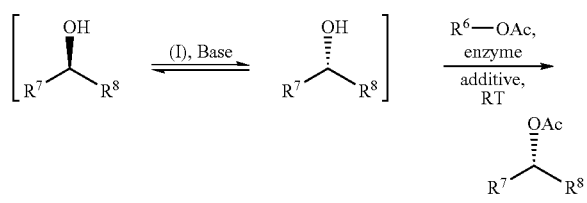

wherein $R^7$ may be $C_{2-8}$ alkyl, $C_{3-7}$ cycloalkyl, phenyl, arylalkyl, aryl-alkenyl, or substituted phenyl;

$R^8$ may be $C_{1-5}$ alkyl, substituted $C_{1-5}$ alkyl or $C_{2-5}$ alkenyl, and the substituent of the substituted alkyl is at least one selected from the group consisting of aryl, $C_{1-5}$ alkoxy, halogen, nitro, nitroso, amino, aminocarbamyl, hydroxy, mercapto and $C_{1-5}$ alkylthio.

Specifically, a racemate form of a chiral alcohol is dissolved into a solvent, together with a ruthenium complex of formula(I), a base, an enzyme catalyst, an acylating agent and an optional additive, and the resulting mixture is simply stirred. After the completion of the reaction, the solution is filtered to remove the enzyme and ruthenium catalysts therefrom, and the desired enantiomeric product is isolated, e.g., by column chromatography.

During the resolution process, the ruthenium catalyst functions to maintain an equilibrium between the enantiomeric forms through facilitating racemization in the presence of a base, while the enzyme effectuates selective acylation of one of the enantiomeric forms into an enantiomerically pure compound at a rate which is substantially greater than the rate of reaction of the other enantiomeric form. Hence, such resolution process is often referred to as a kinetic resolution process.

In the above reaction, the ruthenium complex may be employed in an amount ranging from $10^{-6}$ to 0.05 molar equivalent, the base may be employed in amount ranging from $10^{-6}$ to 0.06 molar equivalent, the acylating agent may be employed in an amount ranging from 1 to 5 molar equivalents, and the optional additive may be employed in an amount ranging from 0.5 to 2 molar equivalents, based on the racemic alcohol, respectively, and the enzyme may be added in an effective catalytic amount.

The above reaction may be conducted at a temperature at which the enzyme is active, e.g., from 0 to 120° C. under an inert gas atmosphere, and the resulting reaction product was concentrated and purified by column chromatography to obtain the chiral acetate.

The base used with the ruthenium catalyst in the above reaction may be an inorganic base such as LiOH, KOH, NaOH, potassium t-butoxide (t-BuOK) and $Na_2CO_3$, or an organic base such as triethylamine, diisopropylethylamine, DBU(1,8-diazabicyclo[5.4.0]undec-7-ene), DBN(1,5-diazabicyclo[4.3.0]non-5-ene).

Further, the enzyme catalyst may be used in a natural or immobilized form, and it is preferably a lipase, which is widely used in the preparation of an optically active compounds. Representative examples of the lipase may include *Pseudomonas cepacia* lipase(LPS), *Candida antarctica* lipase(CAL), *Candida rugosa* lipase(CRL), *Candida cylindracea* lipase(CCL), *Aspergillus niger* lipase(ANL), *Mucor miehei* lipase, *Pseudomonas fluorecens* lipase(LAK), *Rhizopus arrhizus* lipase, *Rhizopus niveus* lipase, Hog pancreas lipase, *Candida lipolytica* lipase, *Mucor javanicus* lipase, *Penicillium roqueforti* lipase, and *Rhizomucor miehei* lipase.

Optionally, an additive may be further added in the above reaction and representative examples of the optional additive may include LiOH, $Na_2CO_3$, triethylamine, diisopropylethylamine, and a molecular sieve.

The solvent which may be preferably used in the above reaction is an aprotic solvent and representative examples of the aprotic solvent include toluene, hexane, benzene, tetrahydrofuran, dioxane, dialkyl ether, alkyl acetate, acetonitrile, acetone, dichloromethane, chloroform and carbon tetrachloride, and, in addition, a water-immiscible alcohol having four or more carbon atoms may also be used.

The following Examples are given for the purpose of illustration only and are not intended to limit the scope of the invention.

Systhesis of Ruthenium Complexes

PREPARATION EXAMPLE 1

Synthesis of N-isobutylamino-2,3,4,5-tetraphenylcyclopentadienyl ruthenium dicarbonyl chloride Step 1) Synthesis of N-isobutyl-2,3,4,5-tetraphenylcyclopentadieneimine 3 g (7.8 mmol) of tetraphenylcyclopentadienone and 3.49 ml (35.1 mmol) of isobutylamine were dissolved in 50 ml of toluene and 0.7 ml (5.85 mmol) of $TiCl_4$ was added thereto at 0° C. The resulting mixture was agitated for 30 minutes at room temperature and then refluxed for 12 hours. The reaction mixture was cooled and diethyl ether was added thereto to induce solid precipitation. The resultant solid was filtered and dried to obtain 2.3 g of the title compound.

m.p.: 158° C.;
$^1H$ NMR($CDCl_3$): 7.25–7.18 (m, 10H), 7.09–7.00(m, 6H), 6.85(d, J=6.6 Hz, 2H), 6.78(m, J=6.6 Hz, 2H), 3.36(d, J=6.5 Hz, 8H), 1.83(m, 1H), 0.79(d, J=6.6 Hz, 2H)

Step 2) Synthesis of N-isobutylamino-2,3,4,5-tetraphenyl-cyclopentadienyl ruthenium dicarbonyl chloride 1 g (2.4 mmol) of the compound prepared in Step 1 and 1 g (1.6 mmol) of $Ru_3(CO)_{12}$ were dissolved in 8 ml of chloroform and reacted under an argon atmosphere at 90° C. for 5 days. The reaction mixture was cooled, concentrated and the residue was purified by column chromatography (column: silica gel, eluent: from hexane/ethylacetate of 8:1 to dichloromethane; gradient) to obtain 0.7 g of the title compound m.p.: 151~152° C. (dec.);
$^1H$ NMR($CDCl_3$): 7.58–7.56(m, 4H), 7.38–7.33(m, 6H), 7.09(dd, J=7.1 Hz, 2H), 7.02–7.91(m, 8H), 4.36(t, J=5.7 Hz, 1H), 2.56(t, J=6.4, 2H), 1.39(m, 1H), 0.57(d, J=6.7 Hz, 6H);
$^{13}C$ NMR($CDCl_3$): 198.6, 144.1, 133.7, 132.1, 130.7, 130.6, 129.1, 128.9, 128.4, 127.9, 101.6, 83.7, 52.1, 29.3, 20.1

PREPARATION EXAMPLE 2

Synthesis of N-isopropylamino-2,3,4,5-tetraphenyl-cyclopentadienyl ruthenium dicarbonyl chloride Step 1) Synthesis of N-isopropyl-2,3,4,5-tetraphenylcyclopentadieneimine The procedure of Step 1 of Preparation Example 1 was repeated using 2.1 g of isopropylamine in place of isobutylamine to obtain the title compound.

m.p.: 223° C.;
$^1H$ NMR($CDCl_3$): 7.25–6.75 (m, 20H), 4.08–4.00 (m, 1H), 1.04(d, J=3 Hz, 6H);
$^{13}C$ NMR($CDCl_3$): 165.8, 137.6, 131.9, 130.2, 129.8, 128.2, 127.8, 127.4, 127.2, 127.1, 126.5, 52.3, 24.3

Step 2) Synthesis of N-isopropylamino-2,3,4,5-tetraphenylcyclopentadienyl ruthenium dicarbonyl chloride The procedure of Step 2 of Preparation Example 1 was repeated using the compound prepared in Step 1 to obtain the title compound.

m.p.: 197° C. (dec.);
$^1H$ NMR($CDCl_3$): 7.57–6.91(m, 20H), 4.20(d, J=4.1 Hz, 1H), 3.3–3.23(m, 1H), 0.86(d, J=3.2 Hz, 6H);
$^{13}C$ NMR($CDCl_3$): 198.4, 144.8, 133.7, 131.9, 130.6, 128.9, 128.7, 128.2, 127.7, 101.4, 81.7, 45.6, 25.2

PREPARATION EXAMPLE 3

Synthesis of N-isobutylamino-2,3,4,5-tetraphenylcyclopentadienyl ruthenium dicarbonyl hydride 90 mg (0.14 mmol) of N-isopropyl-2,3,4,5-tetrabutylcyclopentadienyl ruthenium dicarbonyl chloride prepared in Preparation Example 1 and 45 mg (0.42 mmol) of sodium carbonate were dissolved in 6 ml of isopropanol and reacted at 90° C. for 5 hours. The reaction mixture was filtered and the filtrate was concentrated to obtain 83 mg of the title compound.

m.p.: 86.7° C. (dec.);
$^1H$ NMR($C_6D_6$): 7.77(d, J=6.8 Hz, 4H), 7.57–7.54(m, 4H), 7.22–7.16(m, 8H), 7.04–7.01(m, 6H), 3.17(t, J=6.9 Hz, 1H), 2.66(t, J=6.5 Hz, 2H), 1.49(m, 1H), 0.82(d, J=6.5 Hz, 6H);
$^{13}C$ NMR($C_6D_6$): 203.6, 133.9, 133.7, 132.9, 131.7, 129.2, 129.0, 128.7, 106.6, 92.1, 61.2, 29.2, 20.8

PREPARATION EXAMPLE 4

Synthesis of N-isopropylamino-2,3,4,5-tetraphenyl-cyclopentadienyl ruthenium dicarbonyl hydride The procedure of Preparation Example 3 was repeated using N-isopropyl-2,3,4,5-tetrapropylcyclopentadienyl ruthenium dicarbonyl chloride prepared in Preparation Example 2 to obtain the title compound.

m.p.: 140° C.(dec.);
$^1H$ NMR($C_6D_6$): 7.57–6.73(m, 20H), 2.99–2.93(m, 1H), 2.57(d, J=4.6 Hz, 1H), −9.14(s, 1H);
$^{13}C$ NMR($C_6D_6$): 203.6, 134.1, 133.4, 132.9, 132.8, 130.2, 129.0, 127.8, 127.1, 106.3, 91.0, 50.1, 21.9

Resolution of Chiral Secondary Alcohols

EXAMPLE 1

1 mmol of 1-phenylethanol, 0.05 molar equivalent of potassium t-butoxide, 1 molar equivalent of $Na_2CO_3$, 0.04 molar equivalent of N-isopropylamino-2,3,4,5-tetrabutylcyclopentadienyl ruthenium dicarbonyl chloride prepared in Preparation Example 2, 1.5 molar equivalent of isopropenyl acetate($CH_2$=$CH(CH_3)OCOCH_3$), based on 1-phenylethanol, and 2.8 mg of immobilized CALB(*Candida antatctica* lipase B) were added to 1 ml of toluene. The resulting mixture was stirred for 30 hours at room temperature under an argon atmosphere. The resulting reaction product was concentrated and purified by a silica gel column chromatography (eluent: dichloromethane/ethyl acetate=8) to obtain(R)-1-phenylethyl acetate having an optical purity of higher than 99% at a yield of 97%.

EXAMPLE 2

The procedure of Example 1 was repeated except that 1 molar equivalent of the compound prepared in Preparation Example 4 was used in place of the compound of Preparation Example 2, to obtain (R)-1-phenylethyl acetate having an optical purity of higher than 98.5% at a yield of 88%.

EXAMPLE 3

The procedure of Example 1 was repeated except that 1-cyclohexylethanol was used instead of 1-phenylethanol, to obtain (R)-1-cyclohexylethyl acetate having an optical purity of higher than 99% at a yield of 86%.

EXAMPLE 4

The procedure of Example 1 was repeated except that 2-octanol was used instead of 1-phenylethanol, to obtain (R)-2-octyl acetate having an optical purity of higher than 91% at a yield of 89%.

EXAMPLE 5

The procedure of Example 1 was repeated except that vinyl acetate ($CH_2=CHOCOCH_3$) was used as an acylating agent instead of isopropenyl acetate over a reaction period of 96 hours, to obtain (R)-1-phenylethyl acetate having an optical purity of higher than 97% at a yield of 89%.

COMPARATIVE EXAMPLE 1

The procedure of Example 1 was repeated except that 3 molar equivalents of p-chlorophenyl acetate (a conventional acylating agent) was used in place of isopropenyl acetate in the presence of three times the amount of the enzyme catalyst used in Example 1 over a reaction period of 42 hours, to obtain (R)-1-phenylethyl acetate having an optical purity of higher than 99%, at a yield of 95%.

The results of Examples 1 to 5 with Comparative Example 1 show that even when an alkenyl acetate is used as an acylating agent in accordance with the present invention, a desired enantiomer can be effectively resolved from its racemate at a yield comparable to that obtained using an aryl acetate that gives an aryl alcohol by-product which is difficult to separate from the reaction product.

EXAMPLE 6

The procedure of Example 1 was repeated except that vinyl acetate ($CH_2=CHOCOCH_3$) was used as an acylating agent in the absence of added $Na_2CO_3$ over a reaction period of 96 hours, to obtain (R)-1-phenylethyl acetate having an optical purity of higher than 98.6% at a yield of 55%.

EXAMPLE 7

The procedure of Example 1 was repeated except that 60 mg of Molecular Sieve 4A was employed instead of $Na_2CO_3$ over a reaction period of 96 hours, to obtain (R)-1-phenylethyl acetate having an optical purity of higher than 98.5% at a yield of 98%.

EXAMPLE 8

The procedure of Example 1 was repeated except that the reaction was conducted at 40° C. for 24 hours, to obtain (R)-1-phenylethyl acetate having an optical purity of higher than 99% at a yield of 95%.

EXAMPLE 9

The procedure of Example 1 was repeated except that the reaction was conducted at 70° C. for 12 hours, to obtain (R)-1-phenylethyl acetate having an optical purity of higher than 99% at a yield of 90%.

As the results of the above Examples show, in accordance with the present invention, a chiral alcohol can be efficiently resolved when the inventive aminocyclopentadienyl ruthenium catalyst is used under a mild condition in the presence of an appropriate enzymes and an alkenyl acetate.

While the invention has been described in connection with the above specific embodiments, it should be recognized that various modifications and changes may be made to the invention by those skilled in the art without departing from the scope of the invention as defined by the appended claims.

What is claimed is:

1. A method of resolving a chiral compound comprising reacting the chiral compound with an acylating agent in the presence of a metal catalyst, an enzyme catalyst, and a base, characterized in that the metal catalyst is a ruthenium complex of formula(I):

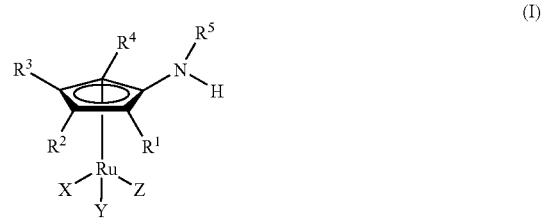

wherein:
$R^1$, $R^2$, $R^3$ and $R^4$ are each independently phenyl, substituted phenyl or $C_{1-5}$ alkyl;
$R^5$ is hydrogen, phenyl, substituted phenyl, $C_{1-5}$ alkyl, substituted $C_{1-5}$ alkyl, $C_{3-7}$ cycloalkyl, $C_{2-5}$ alkenyl or $C_{2-5}$ alkynyl; and
X, Y and Z are each independently hydrogen, halogen, carbonyl or $PR^5_3$.

2. The method of claim 1, wherein the acylating agent is a compound of formula

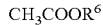

wherein:
$R^6$ is a $C_{2-5}$ alkenyl or substituted $C_{2-5}$ alkenyl.

3. The method of claim 1, wherein the chiral compound is a chiral secondary alcohol.

4. The method of claim 1, wherein the substituent of the substituted phenyl is at least one selected from the group consisting of $C_{1-5}$ alkyl, cycloalkyl, alkenyl, alkynyl, alkoxy, halogen, nitro, nitroso, amino, aminocarbamyl, hydroxy, mercapto and $C_{1-5}$ alkylthio and the substituent of the substituted $C_{1-5}$ alkyl is at least one selected from the group consisting of aryl, $C_{1-5}$ alkoxy, halogen, nitro, nitroso, amino, aminocarbamyl, hydroxy, mercapto and $C_{1-5}$ alkylthio.

5. The method of claim 1, wherein $R^1$, $R^2$, $R^3$ and $R^4$ are each independently phenyl or $C_{1-5}$ alkyl; $R^5$ is hydrogen, phenyl, $C_{1-5}$ alkyl or $C_{3-7}$ cycloalkyl; and X, Y and Z are each independently hydrogen, halogen, carbonyl or phospine.

6. The method of claim 1, wherein the enzyme catalyst is a natural or immobilized lipase.

7. The method of claim 6, wherein the lipase is selected from the group consisting of *Pseudomonas cepacia* lipase (LPS), *Candida antarctica* lipase(CAL), *Candida rugosa* lipase(CRL), *Candida cylindracea* lipase(CCL), *Aspergillus niger* lipase(ANL), *Mucor miehei* lipase, *Pseudomonas fluorecens* lipase(LAK), *Rhizopus arrhizus* lipase, *Rhizopus*

*niveus* lipase, Hog pancreas lipase, *Candida lipolytica* lipase, *Mucor javanicus* lipase, *Penicillium roqueforti* lipase, and *Rhizomucor miehei* lipase, and a combination thereof.

8. The method of claim 1, wherein the base is an inorganic base selected from the group consisting of LiOH, KOH, NaOH, potassium t-butoxide(t-BuOK) and $Na_2CO_3$, or an organic base selected from the group consisting of triethylamine, diisopropylethylamine, DBU(1,8-diazabicyclo[5.4.0]undec-7-ene) and DBN(1,5-diazabicyclo[4.3.0] non-5-ene).

9. The method of claim 1, wherein the reaction is conducted in a solvent selected from the group consisting of toluene, hexane, benzene, tetrahydrofuran, dioxane, dialkyl ether, alkyl acetate, acetonitrile, acetone, dichloromethane, chloroform, carbon tetrachloride and $C_{4-10}$ alcohol.

10. The method of claim 1, wherein an additive selected from the group consisting of LiOH, $Na_2CO_3$, triethylamine, diisopropylethylamine, and a molecular sieve is further added in the reaction.

11. The method of claim 1, wherein the reaction is conducted at a temperature ranging from 0 to 120° C. under an inert gas atmosphere.

* * * * *